US006615848B2

(12) United States Patent
Coats

(10) Patent No.: US 6,615,848 B2
(45) Date of Patent: Sep. 9, 2003

(54) ELECTRONICALLY CONTROLLED PIPELINE MONITORING AND CLEANING DEVICE

(75) Inventor: E. Alan Coats, The Woodlands, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 10/060,667

(22) Filed: Jan. 30, 2002

(65) Prior Publication Data

US 2003/0140946 A1 Jul. 31, 2003

(51) Int. Cl.[7] .............................. B08B 9/04; B08B 3/02
(52) U.S. Cl. ................................ 134/22.11; 134/22.12; 134/24; 134/113; 134/168 C
(58) Field of Search .................... 134/22.11, 22.12, 134/24, 18, 1, 8, 113, 167 C, 168 C, 169 C, 166 C

(56) References Cited

U.S. PATENT DOCUMENTS

| | | | |
|---|---|---|---|
| 4,457,073 A | 7/1984 | Payne | ......................... 33/178 |
| 4,995,201 A * | 2/1991 | von Borcke et al. | .......... 451/76 |
| 5,088,336 A | 2/1992 | Rosenberg et al. | ......... 73/865.8 |
| 5,130,950 A | 7/1992 | Orban et al. | ................... 367/34 |
| 5,653,819 A * | 8/1997 | Bee et al. | ...................... 134/10 |
| 5,988,188 A * | 11/1999 | Born | ........................ 134/22.11 |
| 6,170,577 B1 | 1/2001 | Noles, Jr. et al. | ............ 166/312 |
| 6,375,757 B2 * | 4/2002 | Gazewood | ................... 134/24 |

* cited by examiner

Primary Examiner—Randy Gulakowski
Assistant Examiner—David Chaudhry
(74) Attorney, Agent, or Firm—Conley Rose, P.C.

(57) ABSTRACT

The methods and apparatus of the present invention include an tubing disposed within an conduit to assure flow through the outer pipe. The tubing string is nearly neutrally buoyant or substantially buoyant and has a cleaning and monitoring tool attached to its end. In a preferred embodiment of the present invention, an apparatus for removing material from an conduit includes an tubing extending through the conduit and having a flowbore adapted to flow fluids within the tubing and a monitoring and cleaning tool attached to and receiving the fluids from the tubing. The tool preferably includes a plurality of nozzles, a sonic measuring device, and an expandable element.

27 Claims, 2 Drawing Sheets

ELECTRONICALLY CONTROLLED PIPELINE MONITORING AND CLEANING DEVICE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The invention relates generally to apparatus and methods used for removing material from inside a conduit. More particularly, the present invention relates to a system capable of monitoring and removing material built-up on the inside surface of, or disposed within, a conduit. Still more particularly, the present invention relates to a tubing conveyed tool used to clean and caliper a flowline, pipeline, or well tubing.

Undesirable materials that build-up, or otherwise collect, on the inside walls of conduits, such as well tubing, injection lines, pipelines, flowlines, boiler tubes, heat exchangers and water lines, are known to restrict or interfere with the desired movement of fluids and equipment through the conduits. As a result, in many cases, the conduit becomes useless, or inoperable for its intended purpose. Conduits used to transport hydrocarbons, or in other oilfield applications, are particularly susceptible to the deposit of undesirable, obstructive materials such as barium sulfate, strontium sulfate, calcium sulfate, calcium carbonate, iron sulfide, other scale precipitates (such as silicates, sulfates, sulfides, fluorides, carbonates), cement corrosion products, deteriorated conduit lining, and dehydrated material (such as drilling fluid).

Current techniques for cleaning conduits used in hydrocarbon or oilfield applications include tubing conveyed cleaning methods and pipeline pigging. Tubing conveyed cleaning methods typically involve running into a conduit a cleaning device disposed on a drill string, where the drill string may be standard drill pipe or coiled tubing. Tubing conveyed cleaning devices have included those that use mechanical means, such as cutting mills, bits, or reamers, and others that use pressurized jets, possibly containing abrasives, to clean deposits from the inside of a conduit.

Various tubing conveyed techniques for conduit cleaning involve the use of a mill or bit to remove obstructive material from conduits. The mill or bit is lowered into a conduit by a string of pipe or tubing and rotated to effectively cut any deposits from the inside of the conduit. In many applications, the mills or bits have a short useful life due to damage from contact between the mills and bits and commonly occurring hard, dense, obstructive materials. Therefore, mills or bits may have to be frequently removed from the conduit and replaced, consuming time and increasing expense. Further, rotation of the mill or bit may require additional component parts, such as a motor, bearings, and rotary seals, which are complex and costly to manufacture and operate and are also subject to failure.

These techniques are also largely ineffective at loosening and removing substantially all obstructive material without damaging the conduit. For example, the inside walls of conduits cleaned with mills or bits are highly subject to damage from contact by the mill or bit. Such contact commonly occurs when the obstructions in the conduit are unevenly dispersed, causing the mill or bit to jam or rub against, or cut into, the inside of the conduit. Further, reactive torque due to the rotation of the mill or bit can also cause it to contact the inside surface of the conduit and cause damage thereto. Such reactive torque may also accelerates deterioration to the tubing, such as coiled tubing, that carries the mill or bit.

Other tubing conveyed cleaning methods utilize jet nozzles that eject liquid or angular-shaped solid particles in a foam or liquid transport medium. These systems typically operate in low to moderate pressure ranges and have often proven ineffective at loosening or removing commonly encountered hard, tightly bonded obstructive materials, such as barium sulfate. Higher pressure systems have been known too damage the inside surface of metal conduits as a result of the angular solids cutting, scarring, and eroding the metal. These systems lack the ability to minimize or control the amount of damage that occurs to the metal conduit; therefore, their use is not entirely satisfactory for many applications.

Tubing conveyed systems also may not be preferred in systems having long horizontal runs because the weight of a steel tubing string may hinder the travel of the cleaning device. The weight of a steel tubing string may cause the string to rest on the inside of the tubing, creating a resistance to moving the tubing relative to the conduit. A steel tubing string may also not be flexible enough to be inserted into a conduit string having high angle bends or other tortuous pathways.

Pipeline pigging is also well known in the art and involves pumping a "pig" through a pipeline. A pig is inserted into a conduit and forms at least a partial seal against the conduit wall so that the pig can be pumped through the pipeline using pressurized fluid. The pig scrapes deposits from the wall as it moves through the conduit. Once the pig reaches the end of a section to be cleaned, it is either removed from the conduit or pumped back to the starting position. Typically, special equipment and installations must be provided to allow access to and from the conduit for the pig at one or more locations on the conduit, which increases capital equipment costs. Pipeline pigging may also be undesirable in applications having heavy deposits, which may prohibit the movement of a pig, or where running and retrieval of a pig is difficult, such as in deep water or harsh environments. Additionally, most prior art pigs are simply pumped through the conduit with no provisions for control or monitoring of the progress of the pig or the status of the conduit bore from the surface.

Thus, there remains a need for a system for loosening and removing undesirable materials built-up, or otherwise collected, on the inside surface of conduits, that allows for remote control and monitoring of the cleaning process. The preferred system is simple, cost-effective, and easy to manufacture and operate. Ideally, the system can utilize and interface with existing equipment. Especially well received would be a system that can quickly remove all, or substantially all, of the deposited materials. Further, it would be beneficial for the system to be capable of recirculating or reusing its cleaning mixture or the constituents of the cleaning mixture.

SUMMARY OF THE PREFERRED EMBODIMENTS

The preferred embodiments provide a system and apparatus for loosening and removing undesirable deposits from the inside surface of conduits while overcoming at least some of the shortcomings of the prior art. The present system does not cause substantial or undesirable damage to the conduit and is simple, cost-effective and easy to manufacture and operate. The present system can utilize and interface with existing equipment.

One preferred embodiment comprises a powered tool that can be passed through a pipe or other conduit for the removal of solids deposited on the inner wall thereof. The tool includes equipment for advancing the tool, measuring the amount of deposited solids, and removing the solids. The tool is mounted to a string of tubing that is preferably nearly neutrally buoyant, or substantially neutrally buoyant, flexible, and is adapted to allow hydraulic and electric communication between the tool and a control location.

One preferred embodiment of an apparatus for advancing the tool includes a selectively expandable body disposed on the outside of the tool and a valve that controls the flow of fluid through the tubing string. In an expanded position, the expandable body contacts the interior wall of the conduit, including any deposits located thereon, and creates at least a partial seal against the wall. In a first position, the valve directs fluid from the tubing string to a location upstream of the tool to create a pressure differential across the expandable body that forces the tool down the conduit. In a second position, the valve directs fluid from the tubing string to a location downstream of the sealing body to create a pressure differential to force the tool out of the conduit.

One preferred embodiment of an apparatus for measuring the amount of deposited solids is a sonic caliper device. A preferred sonic caliper is adapted to transmit sonic signals toward the wall of the conduit and receive the reflected signals. The sonic caliper is coupled to a processor that can determine the thickness of deposits on the inside of the conduit by analyzing the travel time of the sonic signals. It is preferred that the sonic caliper and processor combination be able to provide real-time solid deposit information to an operator or to a control system.

One preferred embodiment of an apparatus for removing the solids includes a plurality of nozzles that are used to direct a high pressure fluid at deposits on the inside of the conduit. The nozzles are preferably adjustable both in direction and magnitude of flow so that the nozzles can be efficiently used to remove deposits from the conduit. Fluid for the nozzles is preferably pumped through the tubing string from the surface and may contain abrasives or chemicals to aid in the removal of deposits.

Thus, the preferred embodiments provide a tubing conveyed system that monitors the inside diameter of a conduit and removes any deposits that may restrict the conduit. The preferred system is conveyed on a string of coiled tubing that is neutrally buoyant and provides for electrical and hydraulic connection between a tool and a control station. The preferred tool uses hydraulic power to remove deposits from the conduit as well as provide a motive force to control the location of the tool in the conduit.

Thus, the present invention comprises a combination of features and advantages that enable it to substantially advance the art associated with conduit and pipeline cleaning apparatus by providing a tubing conveyed system that can be monitored and controlled from the surface, but is capable of use in conduits with long horizontal runs, tight turns, and tortuous pathways. These and various other characteristics and advantages of the present invention will be readily apparent to those skilled in the art upon reading the following detailed description and referring to the accompanying drawings.

BRIEF DESCRIPTION OF THE DRAWINGS

For a detailed description of a preferred embodiment of the invention, reference will now be made to the accompanying drawings wherein.

Figure 1:
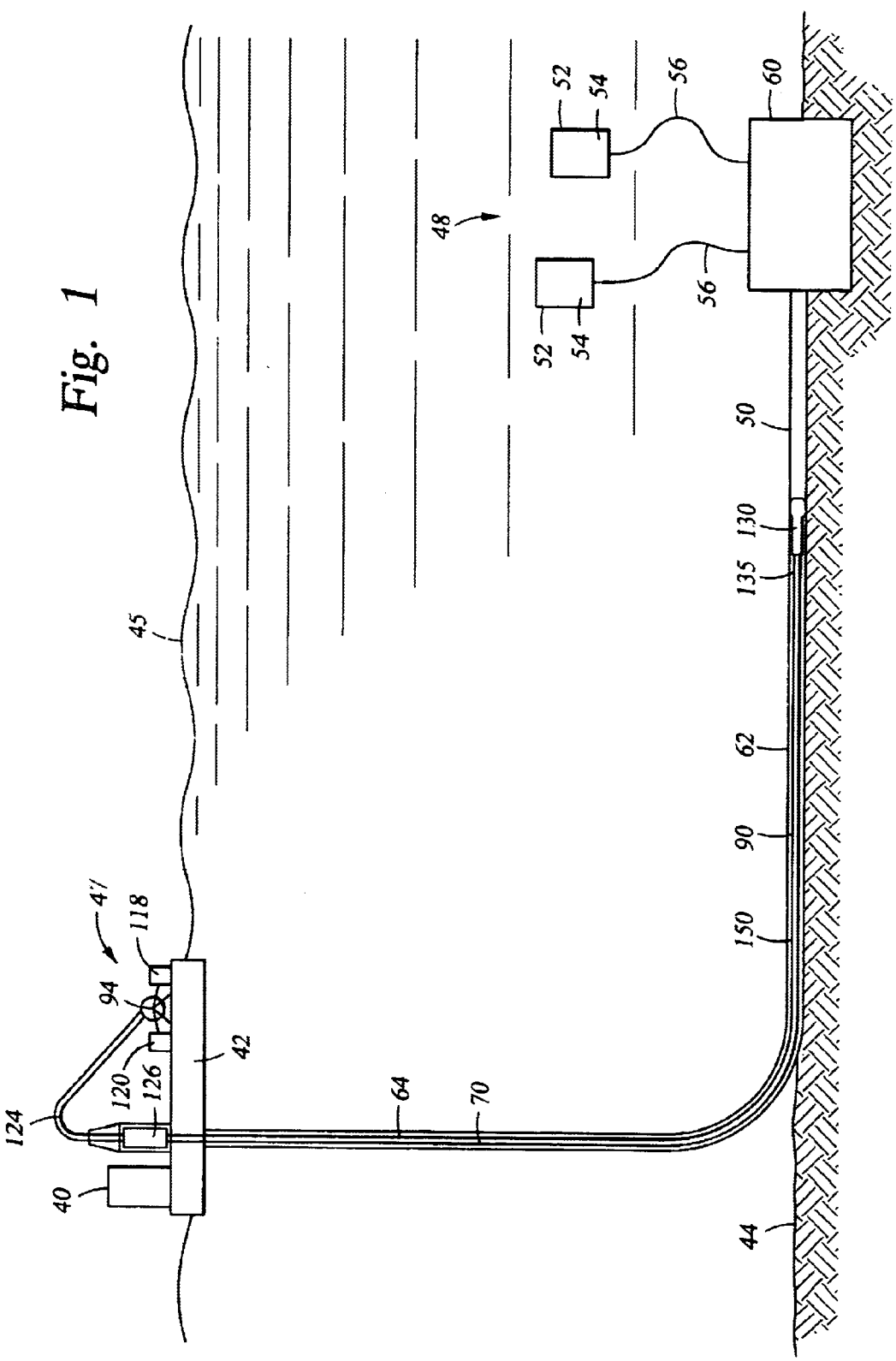
FIG. 1 is an elevational schematic, partly in cross-section, showing an open circuit subsea tieback with a monitoring and cleaning system of the present invention.

The present invention is susceptible to embodiments of different forms. There are shown in the drawings, and herein will be described in detail, specific embodiments of the present invention with the understanding that the present disclosure is to be considered an exemplification of the principles of the invention, and is not intended to limit the invention to that illustrated and described herein.

DESCRIPTION OF PREFERRED EMBODIMENTS

As discussed in detail below, the monitoring and cleaning system of the present invention preferably includes an apparatus for cleaning a conduit, an apparatus for measuring deposits within a conduit, and an apparatus for moving the system through the conduit. The system is preferably disposed at the end of a length of coiled tubing that is buoyant, or near buoyant, within the conduit. Various embodiments of the present invention provide a number of different constructions, each of which is used with a flowline in one of many different types flowline installations and production facilities. The embodiments of the present invention provide a plurality of methods for using the monitoring and cleaning system to assure the flow of well fluids through a flowline. It is to be fully recognized that the different teachings of the embodiments discussed below may be employed in any suitable combination to produce desired results in flow assurance. In particular, the present system may be used in practically any type of new or existing flowline. References to "up" or "down" are made for purposes of ease of description, with "up" meaning upstream toward the surface and "down" meaning downstream toward a well.

The application of the apparatus and methods of the present invention is described in detail with respect to flow assurance in flowlines. However, many of the embodiments may find applications in other types of pipeline systems, such as export pipelines, wellbores, and other tubular constructions susceptible to the deposit of undesirable material.

In the following description, like parts are marked throughout the specification and drawings with the same reference numerals, respectively. The drawing figures are not necessarily to scale. Certain features of the invention may be shown in exaggerated in scale or in somewhat schematic form and some details of conventional elements may not be shown in the interest of clarity and conciseness.

Referring initially to FIG. 1, there is shown an exemplary operating environment for an embodiment of the monitoring and cleaning system of the present invention. A production facility 40 is disposed on a platform 42. Production facility 40 processes well fluids produced from preferably a plurality of fields, such as field 48 including a plurality of producing wells 52, each well 52 having a Christmas tree 54 with an individual flowline 56 extending from each tree 54 to a manifold 60 where the well fluids produced from wells 52 are commingled for transport to production facility 40.

A subsea tie back flowline conduit 50 extends from subsea manifold 60 back to platform 42 and includes a generally horizontal portion 62 connected to, or as an integral part of, a riser portion 64, which extends from the sea floor 44 to the platform 42. Manifold 60 may be located many miles from the production facility 40. It should be appreciated that although only one manifold and flowline are shown for clarity, there may be a plurality of manifolds and producing fields with well fluids being pumped to production facility 40 for processing.

Monitoring and cleaning system 150 is shown disposed within flowline conduit 50 and may be used for a plurality of flow assurance operations, including but not limited to heating the well fluids, reducing the pressure head in the riser 64, dispersing chemicals in the well fluids, such as chemicals to prevent hydrate formation or wax formation, or to remove undesirable buildup in flowline conduit 50.

Monitoring and cleaning system 150 generally includes a surface control station 47 from which tubing string 70 extends into conduit 50 where monitoring and cleaning tool 130 is disposed at the end of tubing string 70. Tubing string 70 may be disposed within flowline 50 at any time during the life of the field 48 and may remain inside flowline 50 for any period such as for hours, days, weeks, months, and years, up to and including the full life of the field 48. Similarly, tubing string 70 may be inserted any distance into flowline 50. Tubing string 70 needs be installed only a sufficient length in flowline 50 and at a predetermined location in flowline 50 to perform the necessary flow assurance functions.

It should be appreciated that tubing string 70 may be installed from a floating vessel and may be inserted at any point along flowline 50. One method of installation is the use of a Swift Riser described in U.S. patent application Ser. No. 09/444,598 filed Jan. 18, 2000 and entitled "A System for Accessing Oil Wells with Compliant Guide and Coiled Tubing." The Swift Riser is a method that allows the injection into the flowline from a reel on the vessel.

Referring again to FIG. 1, the upper end of tubing 70 is connected to a power supply 118 and to a surface processor 120 at the platform. Its downhole end is connected to the monitoring and cleaning tool 130, hereinafter described, for conducting a flow assurance operation within flowline 50. Tubing 17 preferably provides both power and command signals to monitoring and cleaning tool 130 as well as providing for "real time" communication of data from tool 130 to surface processor 120.

At the surface 45, an operational system 47 includes power supply 118, surface processor 120, and a powered coiled tubing spool or reel 94. Surface processor 120 provides electrical power and control, while power supply 118 provides hydraulic power supply through tubing 70 to tool 130. Powered reel 94 feeds the tubing 70 over a guide 124 and into an injector unit 126, which may include blowout preventers. Although FIG. 1 illustrates installing coiled tubing 80 from platform 42, it should be appreciated that coiled tubing 80 may be injected into any point in flowline 50 using standard coiled tubing installation techniques.

Tubing string 70 is preferably a coiled tubing, as hereinafter described, and is preferred because it obviates the need for multiple connections that are required when jointed pipe is used. It is preferred that tubing string 70 and its contents, taken together, be nearly neutrally buoyant or fully neutrally buoyant wherein the fluid contents of flowline 50, so that tubing 70 and its contents have substantially the same density as the fluids around it in flowline 50.

If tubing string 70 is made substantially buoyant, the weight of tubing string 70 in the fluid-filled flowline 50 becomes nil and tubing string 70 will not bear on the inner surface of flow line 50. It should be appreciated that tubing string 70 can only be substantially neutrally buoyant, since buoyancy will change with changes to the well fluids and may be different at different locations of flowline 50. Reducing the friction between tubing string 70 and flowline 50 reduces the friction therebetween and thus facilitates movement of tubing string 70 relative to flowline 50. Therefore, tubing string 70 preferably is made of a composite that lends itself to be buoyant in the fluids in flowline 50. However, metal jointed pipe or metal coiled tubing may also be made substantially buoyant such as by adding buoyancy to the metal pipe.

Figure 2:
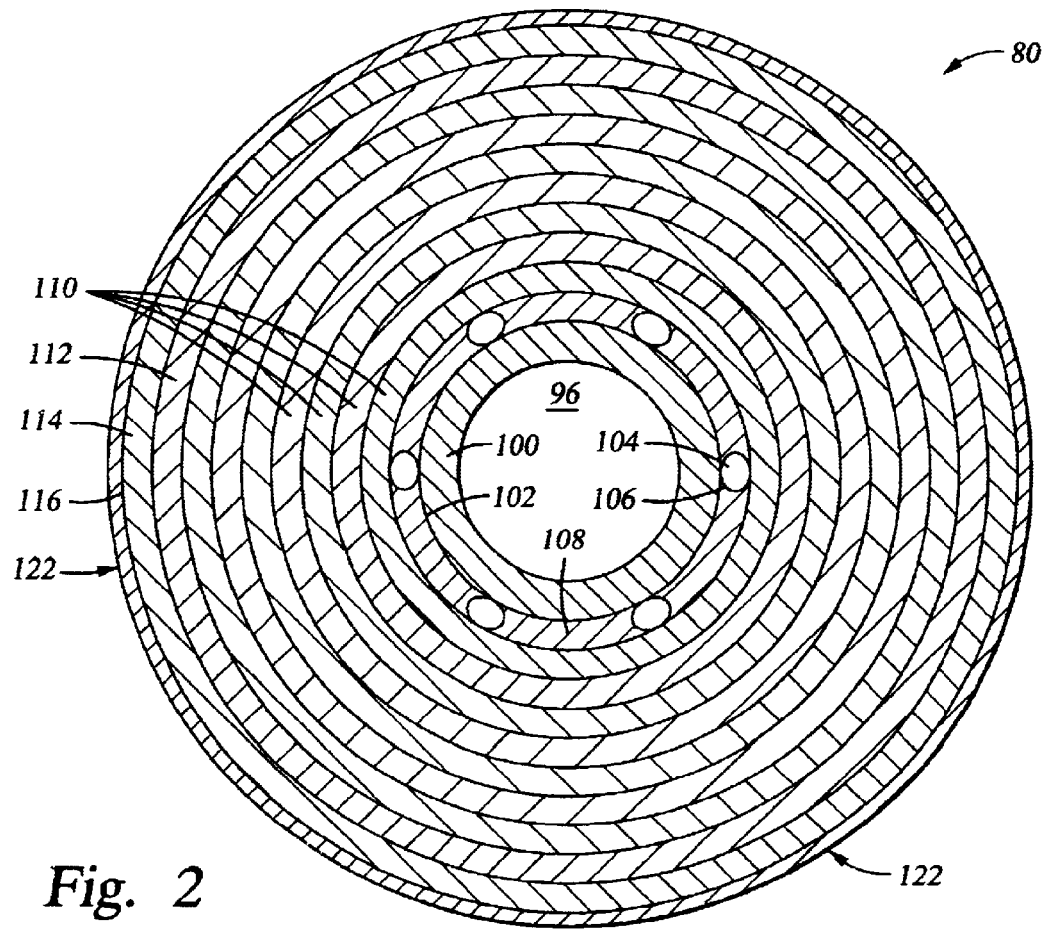
FIG. 2 is a cross-section of coiled tubing with conductors in the wall thereof where the coiled tubing is the continuous tubing string of FIG. 1.

Referring to FIG. 2, a preferred composite coiled tubing 80 preferably includes a tube made of a composite material and including an impermeable fluid liner 100, a layer of glass fiber 102, a plurality of conductors 104 and fiber optic cables 106 around the liner 100 and glass layer 102 embedded in a protective resin 108, a plurality of load carrying layers 110 forming a carbon fiber matrix, a wear layer 112, a layer of polyvinylidene fluoride (PVDF) 114, and an outer wear layer 116 formed of glass fibers. Impermeable fluid liner 100 is an inner tube preferably made of a polymer, such as polyvinyl chloride or polyethylene, or any other material which can withstand the chemicals used for flow assurance and the temperatures of any hot liquids flowing through flowbore 96. The inner liner 100 is impermeable to fluids and thereby isolates the load carrying layers 110 from the chemicals and/or hot liquids passing through the flow bore 96 of liner 100. The load carrying layers 110 are preferably a resin fiber having a sufficient number of layers to sustain the required load of the tubing string 70, particularly during installation. The wear layer 112 is preferably an outer load carrying layer and, although only one wear layer 116 is shown, there may be additional wear layers as required. The PVDF layer 114 is impermeable to well fluids and isolates the load carrying layers 110 while outermost wear layer 116 is a sacrificial layer. Composite coiled tubing is also described in U.S. patent application Ser. No. 09/081,961 filed May 20, 1998 and entitled "Well System", and in U.S. Provisional Patent Application Serial No. 60/323,917 filed Sep. 21, 2001 and entitled "Methods and Apparatus for a Subsea Tie Back", hereby incorporated herein by reference.

As described above, tubing 70 preferably includes conductors 104 and/or cables 106 in the wall of tubing string 70. It should be appreciated that other configurations of composite tubing as well as metal coiled tubing may also include conductors and fiber optics mounted on the interior or exterior of the metal coiled tubing.

Figure 3:
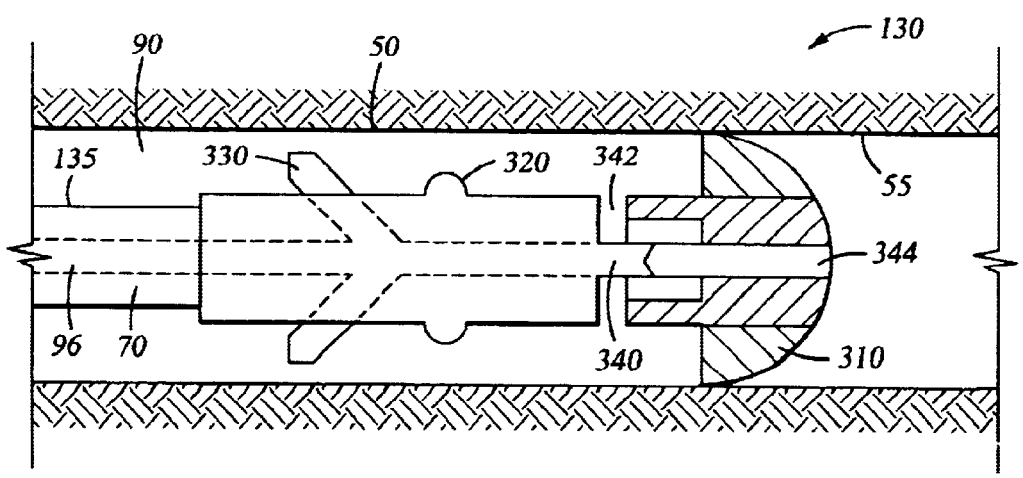
FIG. 3 is cross-section of a monitoring and cleaning tool in accordance with a preferred embodiment of the present invention.

Referring now to FIG. 3, a preferred embodiment of the present monitoring and cleaning tool 130 includes radially expandable element 310 for moving tool 130 through a conduit, sonic measuring device 320 for measuring the amount of deposits in the conduit, and electronically actuated nozzles 330 for removing the deposits from the conduit. Tool 130 is preferably located at the end 135 of tubing 70 but may be adapted to attach to further lengths of tubing so as to allow for a plurality of tools 130 to be attached along the length of tubing string 70.

To install tubing 70 any appreciable distance within flowline 50, as for example several miles, it is preferable to provide a motive means at the remote end of tubing 70. Expandable element 310 is one embodiment of an apparatus for providing this motive means. In a preferred embodiment, expandable element 310 is an electronically controlled elastomer. Element 310 may be a sealing element such as those used in current packer and pig technology and may be expanded by hydraulic or mechanical means. In another embodiment, element 310 is preferably omni-directional and is inflated with fluid flowing through tubing string 70. The collection of fluid in element 310 forces it to expand into sealing contact with inner surface 55 of flowline 50. Thus, sealing contact can be established at any point along flowline 50. Element 310 may also include packer cups, wash cups, and swab cups. In some embodiments, the packer cups may be fluted.

Expandable element 310 serves as a flow restriction member at the end 135 of tubing 70. In one embodiment, fluid is pumped through annulus 90, between tubing string 70 and flowline 50 to create a pressure differential across the element 310 applies a motive force to element 310 and in turn to tubing 70. In another embodiment, fluid is pumped through tubing 70 where the flow of fluid is controlled by valve 340. Valve 340 is preferably a sleeve valve that in a first position directs the flow behind element 310 via outlet 342 and in a second position directs the flow in front of element 310 via outlet 344. Thus, tubing string 70 and tool 130 can be pumped into or out of flowline 50 as desired.

Still referring to FIG. 3, the present tool 130 further includes at least one and preferably a plurality of electronically actuated nozzles 330. Nozzles 330 are in fluid communication with flowbore 96 through tubing string 70 and are used to blast deposits and scale off of flowline walls. Any desirable quantity, size, orientation, and configuration of nozzles (i.e. conventional nozzles, vortex nozzles) capable of removing obstructions may be used. Nozzles 330 are preferably moveable so as to be directed at an area of deposits. One preferred fluid for ejection through nozzles 330 is stabilized crude, i.e. well fluids that have been processed at production facility 40. The processed crude can be heated and recirculated through the tubing 70 and back up the annulus 90 between the tubing 70 and flowline 50.

Tubing string 70 and nozzles 330 of tool 130 may also be open such that any fluids being pumped through tubing string 70 will flow into the annulus 90 of flowline 50 via nozzles 330. The fluids exiting nozzles 330 will mix with the fluids in flowline 50 to condition the flowline fluid as desired. In some embodiments, nozzles 330 may be located in front of expandable element 310, allowing the fluids to flow into the flowbore 92. In this manner, various chemicals, such as methanol, can be pumped down the tubing string 70 to mix with fluids in flowline 50. Chemicals may be needed for a variety of reasons to condition the fluids in flowline 50, including corrosion inhibition, wax removal, and hydrate formation removal. See U.S. patent application Ser. No. 09/377,982 filed Aug. 20, 1999 and entitled "Electrical Surface Activated Downhole Circulating Sub," which is incorporated herein by reference.

Still referring to FIG. 3, the present tool 130 preferably includes a sonic measuring device 320 that monitors the condition of flowline 50 before and/or after it is cleaned. In a preferred embodiment, sonic measuring device measures 320 measures, or calipers, the internal diameter of the flowline using known sonic calipering techniques. Sonic measuring device 320 may operate in the subsonic to supersonic frequencies, depending upon the medium through which it is travelling.

A preferred sonic measuring device 320 includes a plurality of sonic transducers, or a combination of transmitters and receivers, disposed on tool 130. Device 320 transmits a sonic signal through the fluid in the conduit toward the wall. A portion of the signal is reflected off of any surface encountered by the signal, such as a layer of deposits or the wall of the conduit. This signal is then received by device 320. Device 320 is coupled to a processor (not shown) that may be integral to the tool or in a remote location. The processor controls the transmission of signals from device 320 and monitors the time it takes for the signal to return to the receiver. Using known values for the speed of the sonic signal in the fluid the processor can determine the distance from device 320 to the wall of the conduit or a layer of deposits thereon.

A preferred sonic measuring device 320 would employ a sonic signal capable of penetrating a layer of deposits so that the receiver would receive both a reflected signal from the deposit layer and a reflected signal from the wall of the conduit. By receiving both reflected signals, device 320, including a processor, is able to determine the thickness of a layer of deposits as well as the actual inner diameter of the conduit. Thus, sonic measuring device 320 could not only be used to locate deposits of solids but also to monitor any decreasing wall thickness in the conduit due to corrosion or erosion.

Referring now to FIGS. 1 and 3, monitoring and cleaning system 150 preferably comprises surface control station 47, tubing string 70, and monitoring and cleaning tool 130. In operation, once monitoring and cleaning system 150 is deployed in flowline 50, expandable element 310 of tool 130 is inflated to sealingly contact inner surface 55 of flowline 50, as described above. Fluid pressure against the element 310 provides the motive force to propel tubing string 70 within flowline 50. Initially, the fluid flow may be directed behind the elastomeric seal by sleeve valve 340.

As system 150 moves through flowline 50, nozzles 330 jet chemicals against inner surface 55 break up any debris and sonic measuring device 320 measures at least the reduced inner diameter of flowline 50. Once a sufficient length of pipe has been cleaned, sleeve valve 340 directs the fluid flow in front of the elastomeric seal, forcing the system 150 to travel in the opposite direction. Alternatively, tool 130, along with tubing 70, can be pulled from the well by equipment at the surface, i.e. the coiled tubing reel. Nozzles 330 may or may not jet chemicals, while sonic measuring device 320 measures at least the increased inner diameter of flowline 50.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. For example, the components of the monitoring and cleaning system may be arranged in any order. Accordingly, the scope of protection is not limited to the embodiments described herein, but is only limited by the claims that follow, the scope of which shall include all equivalents of the subject matter of the claims.

What is claimed is:

1. An apparatus for removing material from a conduit, the apparatus comprising:

tubing extending through the conduit and having a flowbore adapted to flow fluids within said tubing, said tubing being nearly neutrally buoyant or substantially neutrally buoyant; and a monitoring and cleaning tool attached to and receiving said fluids from the tubing, the tool comprising:

a plurality of nozzles;

a sonic measuring device; and
an expandable element.

2. The apparatus of claim 1 wherein the conduit is coiled tubing.

3. The apparatus of claim 2 wherein the coiled tubing is composite coiled tubing.

4. The apparatus of claim 3 wherein said composite coiled tubing includes conductors passing through the wall of said composite coiled tubing.

5. The apparatus of claim 1 wherein the plurality of nozzles are electronically actuated.

6. The apparatus of claim 5 wherein the nozzles jet said fluids against the conduit's inner walls.

7. The apparatus of claim 1 wherein the sonic measuring device measures the conduit's inner diameter.

8. The apparatus of claim 1 wherein the expandable element is an elastomer.

9. The apparatus of claim 8 wherein the elastomer is electronically controlled.

10. The apparatus of claim 9 wherein the elastomer is omni-directional.

11. The apparatus of claim 9 wherein the elastomer is inflated with said fluid flowing through said tubing.

12. The apparatus of claim 1 wherein said monitoring and cleaning tool further comprises a valve that selectively controls the movement of the tool through the conduit.

13. The apparatus of claim 12 wherein said valve has a first position and a second position where the position of said valve determines the direction said tool moves through the conduit.

14. The apparatus of claim 13 wherein-said tool moves farther into the conduit with said valve in the first position.

15. The apparatus of claim 13 wherein said tool moves out of the conduit with said valve in the second position.

16. A tool for removing deposits from the inside diameter of a conduit, the tool comprising:
a means for moving the tool through the conduit;
a means for measuring an inner diameter of the conduit; and
a means for removing deposits from the conduit.

17. The tool of claim 16 wherein said means for moving the tool through the conduit utilizes a pressure differential to move the tool.

18. The tool of claim 17 wherein said means for moving the tool through the conduit utilizes an expandable element to restrict flow through the conduit.

19. The tool of claim 18 wherein said means for moving the tool through the conduit includes a valve that controls the pressure differential across the expandable element.

20. The tool of claim 16 wherein said means for measuring an inner diameter utilizes sonic signals.

21. The tool of claim 16 wherein said means for removing deposits utilizes pressurized fluid.

22. A method for monitoring and cleaning a conduit inner diameter with deposits, the method comprising:
disposing into the conduit a tool attached to a tubing string;
measuring the inner diameter of the conduit using a measuring device disposed on the tool;
monitoring the measured diameter of the conduit from a remote location by way of signals transmitted along the tubing string; and
cleaning the inner diameter of the conduit using a cleaning device disposed on the tool.

23. The method of claim 22 further comprising adjusting the position of the tool in the conduit by way of a motive device disposed on the tool.

24. The method of claim 22 wherein the tubing string is substantially buoyant.

25. The method of claim 22 wherein the tubing string is a composite coiled tubing.

26. The method of claim 22 wherein measuring the inner diameter comprises transmitting a sonic signal toward the wall of the conduit and receiving the reflected sonic signal from the wall of the conduit.

27. The method of claim 22 wherein the inner diameter of the conduit is cleaned by pressurized fluid.

* * * * *